United States Patent
Kim et al.

(10) Patent No.: US 9,928,600 B2
(45) Date of Patent: Mar. 27, 2018

(54) COMPUTER-AIDED DIAGNOSIS APPARATUS AND COMPUTER-AIDED DIAGNOSIS METHOD

(71) Applicant: SAMSUNG ELECTRONICS CO., LTD., Suwon-si (KR)

(72) Inventors: Won Sik Kim, Gunpo-si (KR); Ha Young Kim, Yongin-si (KR); Hye Jin Kam, Seongnam-si (KR); Hyo A Kang, Seoul (KR); Joo Hyuk Jeon, Seoul (KR); Seung Chul Chae, Seoul (KR); Seung Woo Ryu, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 58 days.

(21) Appl. No.: 14/966,118

(22) Filed: Dec. 11, 2015

(65) Prior Publication Data

US 2016/0171708 A1    Jun. 16, 2016

(30) Foreign Application Priority Data

Dec. 11, 2014 (KR) .......................... 10-2014-0178732

(51) Int. Cl.
*G06K 9/00*      (2006.01)
*G06T 7/00*      (2017.01)
(Continued)

(52) U.S. Cl.
CPC .......... *G06T 7/0081* (2013.01); *A61B 8/5223* (2013.01); *A61B 8/5246* (2013.01); *A61B 8/5292* (2013.01); *G06F 19/321* (2013.01); *G06F 19/345* (2013.01); *G06T 7/0012* (2013.01); *G06T 7/11* (2017.01); *G06T 7/20* (2013.01); *G06T 2207/30004* (2013.01)

(58) Field of Classification Search
None
See application file for complete search history.

(56) References Cited

U.S. PATENT DOCUMENTS 5,910,114 A     6/1999  Nock et al.
8,031,917 B2 *  10/2011 Lakare .................. G06F 19/321
                                              382/128
(Continued)

FOREIGN PATENT DOCUMENTS

EP          2733669 A2     5/2014

OTHER PUBLICATIONS

Communication dated Nov. 8, 2017, issued by the European Patent Office in counterpart European Patent Application No. 15199299.7.

*Primary Examiner* — Hadi Akhavannik
(74) *Attorney, Agent, or Firm* — Sughrue Mion, PLLC

(57) ABSTRACT

A Computer-Aided Diagnosis (CAD) apparatus and a CAD method are provided. The CAD apparatus includes an automatic diagnoser configured to perform automatic diagnosis using an image that is received from a probe, and generate diagnosis information including results of the automatic diagnosis. The CAD apparatus further includes an information determiner configured to determine diagnosis information to be displayed among the generated diagnosis information, based on a manual diagnosis of a user, and a display configured to display the received image and the determined diagnosis information.

18 Claims, 10 Drawing Sheets

(51) Int. Cl.
*G06F 19/00* (2018.01)
*A61B 8/08* (2006.01)
*G06T 7/20* (2017.01)
*G06T 7/11* (2017.01)

(56) References Cited

U.S. PATENT DOCUMENTS

| | | | |
|---|---|---|---|
| 2004/0086158 A1* | 5/2004 | Leichter | G06K 9/033 |
| | | | 382/128 |
| 2005/0102315 A1* | 5/2005 | Krishnan | G06T 7/0012 |
| 2006/0251306 A1* | 11/2006 | Shin | G06T 7/262 |
| | | | 382/128 |
| 2006/0274928 A1 | 12/2006 | Collins et al. | |
| 2011/0123079 A1 | 5/2011 | Gustafson | |
| 2012/0172726 A1* | 7/2012 | Sakai | A61B 8/00 |
| | | | 600/443 |
| 2013/0050239 A1 | 2/2013 | Karssemeijer et al. | |

\* cited by examiner

PROCESS FOR DETECTION OF LESION

PROCESS FOR OBSERVATION OF LESION (b) CLASSIFICATION RESULT (a) SEGMENTATION

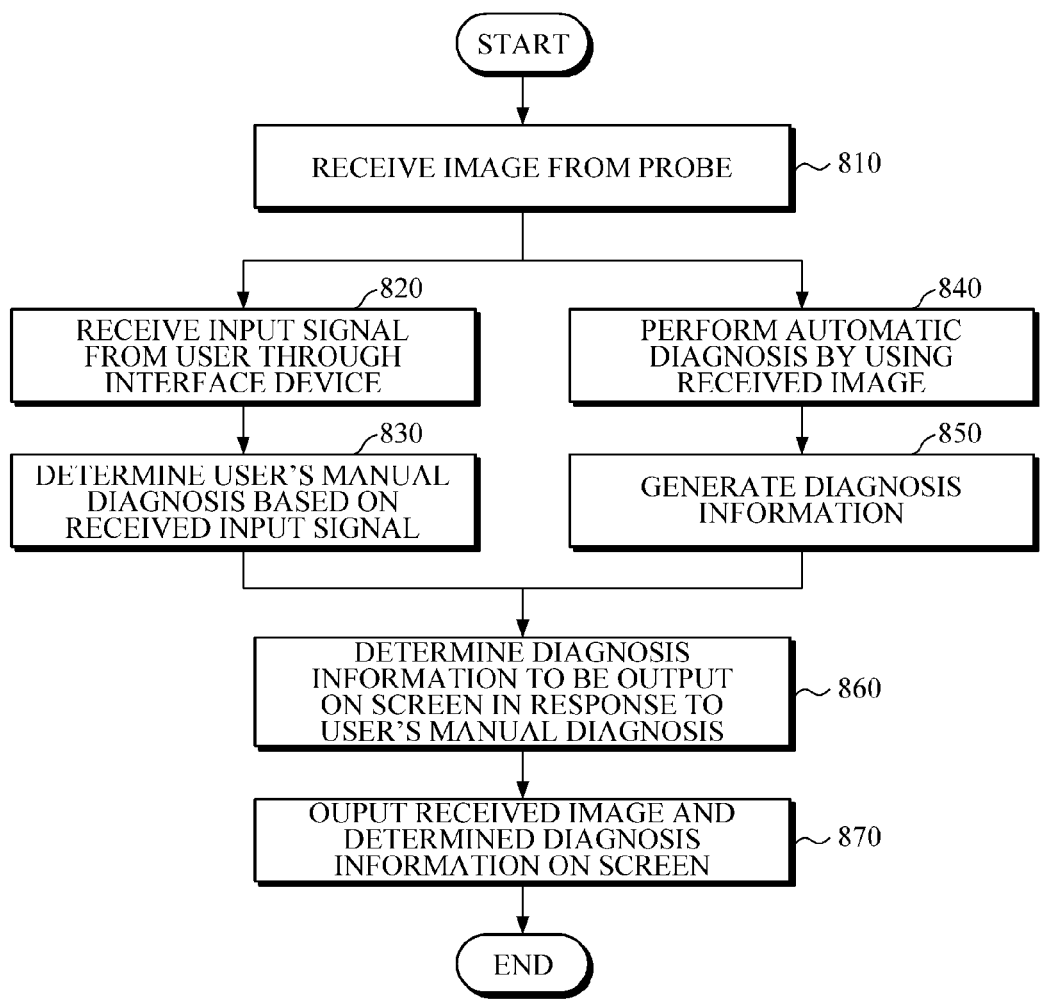

COMPUTER-AIDED DIAGNOSIS APPARATUS AND COMPUTER-AIDED DIAGNOSIS METHOD

CROSS-REFERENCE TO RELATED APPLICATION

This application claims priority from Korean Patent Application No. 10-2014-0178732, filed on Dec. 11, 2014, in the Korean Intellectual Property Office, the entire disclosure of which is incorporated herein by reference in its entirety.

BACKGROUND

1. Field

Apparatuses and methods consistent with exemplary embodiments relate to a Computer-Aided Diagnosis (CAD) apparatus and a CAD method.

2. Description of the Related Art

Computer-aided diagnosis (CAD) systems are used in various applications to help doctors in diagnosis of diseases. For example, ultrasound devices are widely used to help doctors diagnose tumors in the breast. Most of the current CAD systems are used by doctors to locate lesions or to determine whether lesions are malignant or benign by reading images stored therein.

For more efficient diagnosis, there is a demand for a real-time CAD system in which locations of lesions and the like may be identified in real time from videos captured in real time. In the real-time CAD system, computer diagnosis is performed per frame, and various types of information are displayed on a screen to provide information used by doctors. However, such a CAD system that helps doctors in real time by providing all types of information to doctors may hinder diagnosis by doctors.

SUMMARY

Exemplary embodiments address at least the above problems and/or disadvantages and other disadvantages not described above. Also, the exemplary embodiments are not required to overcome the disadvantages described above, and may not overcome any of the problems described above.

According to an aspect of an exemplary embodiment, there is provided a Computer-Aided Diagnosis (CAD) apparatus, including an automatic diagnoser configured to perform automatic diagnosis using an image that is received from a probe, and generate diagnosis information including results of the automatic diagnosis. The CAD apparatus further includes an information determiner configured to determine diagnosis information to be displayed among the generated diagnosis information, based on a manual diagnosis of a user, and a display configured to display the received image and the determined diagnosis information.

The manual diagnosis may include a process for detection of a region of interest (ROI) or a process for observation of the detected ROI.

The information determiner may be configured to in response to the manual diagnosis being the process for the detection of the ROI, determine information of the detection of the ROI to be the diagnosis information to be displayed, and in response to the manual diagnosis being the process for the observation of the detected ROI, determine information of the observation of the detected ROI to be the diagnosis information to be displayed.

In response to the information determiner determining the information of the detection of the ROI to be the diagnosis information to be displayed, the display may be configured to display, on the displayed image, a distinguished marker indicating the detected ROI, based on location information of the detected ROI included in the information of the detection of the ROI.

In response to the information determiner determining the information of the observation of the detected ROI to be the diagnosis information to be displayed, the display may be configured to display the information of the observation of the detected ROI based on types and an output order of the information of the observation of the detected ROI.

The types and the output order may be determined based on at least one among a speed of the probe, an input signal, and a unit of time.

The types may include ROI classification information including a size of the detected ROI, characteristics of the detected ROI, and determination of benignancy or malignancy, Doppler images, ultrasonic elasticity images, anatomical charts, an examination history of a subject, images of body parts of the subject that are acquired by other devices, and information of similar cases.

The CAD apparatus may further include a probe speed detector configured to detect the speed of the probe based on the received image, and determine the manual diagnosis based on the detected speed of the probe.

The probe speed detector may be configured to detect the speed of the probe based on a change in images that are received from the probe, the change in the images including at least one among a difference in image intensities of pixels between the images, a difference in histograms between the images, a similarity in the histograms between the images, a correlation between the images, and a change in information of salient regions of the images.

The automatic diagnoser may be configured to perform the automatic diagnosis at a same time as the probe speed detector detects the speed of the probe.

The automatic diagnoser may be configured to perform the automatic diagnosis in response to the probe speed detector determining the manual diagnosis.

The CAD apparatus may further include an input signal receiver configured to receive an input signal from the user, and determine the manual diagnosis based on the received input signal.

According to an aspect of another exemplary embodiment, there is provided a CAD method, including performing automatic diagnosis using an image that is received from a probe, generating diagnosis information including results of the automatic diagnosis, determining diagnosis information to be displayed among the generated diagnosis information, based on a manual diagnosis of a user, and displaying the received image and the determined diagnosis information.

The determining may include in response to the manual diagnosis being a process for detection of an ROI, determining information of the detection of the ROI to be the diagnosis information to be displayed, and in response to the manual diagnosis being a process for observation of the detected ROI, determining information of the observation of the detected ROI to be the diagnosis information to be displayed.

In response to the determining the information of the detection of the ROI to be the diagnosis information to be displayed, the displaying may include displaying, on the displayed image, a distinguished marker indicating the detected ROI, based on location information of the detected ROI included in the information of the detection of the ROI.

In response to the determining the information of the observation of the detected ROI to be the diagnosis information to be displayed, the displaying may include displaying the information of the observation of the detected ROI based on types and an output order of the information of the observation of the detected ROI.

The CAD method may further include detecting the speed of the probe based on the received image, and determining the manual diagnosis based on the detected speed of the probe.

The detecting may include detecting the speed of the probe based on a change in images that are received from the probe, the change in the images including at least one among a difference in image intensities of pixels between the images, a difference in histograms between the images, a similarity in the histograms between the images, a correlation between the images, and a change in information of salient regions of the images.

According to an aspect of another exemplary embodiment, there is provided a CAD apparatus, including a diagnoser configured to perform a diagnosis of an image that is received from a probe, a determiner configured to determine information to be displayed among results of the diagnosis, based on at least one among a speed of the probe and a number of input signals that are received from a user, and a display configured to display the received image and the determined information.

BRIEF DESCRIPTION OF THE DRAWINGS

The above and/or other aspects will be more apparent by describing exemplary embodiments, with reference to the accompanying drawings, in which:

FIG. 8 is a flowchart illustrating a CAD method, according to yet another exemplary embodiment.

DETAILED DESCRIPTION

Figure 1:
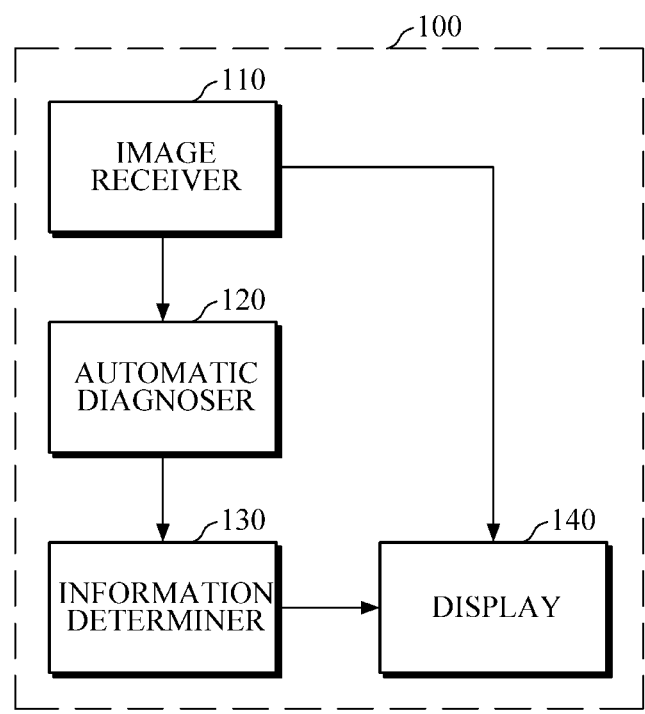
FIG. 1 is a block diagram illustrating a Computer-Aided Diagnosis (CAD) apparatus, according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions may not be described in detail because they would obscure the description with unnecessary detail.

It will be understood that the terms "comprises" and/or "comprising" used herein specify the presence of stated features or components, but do not preclude the presence or addition of one or more other features or components. In addition, the terms such as "unit", "-er (-or)", and "module" described in the specification refer to an element for performing at least one function or operation, and may be implemented in hardware, software, or the combination of hardware and software.

The exemplary embodiments to be described below may be applied to a Computer-Aided Diagnosis (CAD) apparatus that analyzes ultrasound images acquired in real time through a probe to detect regions of interest (ROIs) and to provide diagnosis results on the detected ROIs. However, the exemplary embodiments are not limited thereto, and may also be applied to CAD apparatuses that receive and diagnose medical images acquired by using various techniques, such as Computed Tomography (CT), Magnetic Resonance Imaging (MRI), and the like.

FIG. 1 is a block diagram illustrating a CAD apparatus 100, according to an exemplary embodiment.

Referring to FIG. 1, the CAD apparatus 100 includes an image receiver 110, an automatic diagnoser 120, an information determiner 130, and a display 140.

The image receiver 110 receives images by using a probe. A user presses the probe against an examination region (e.g., abdomen, chest, liver, breast, etc.) of a subject, and moves the probe in various directions to acquire images in real time. The real-time images acquired by the probe may be input to the image receiver 110 in units of frames.

Once the image receiver 110 receives images by using the probe, the automatic diagnoser 120 uses the received images to perform automatic diagnosis. The automatic diagnosis includes detection of ROIs from images, and determination of the detected ROIs.

The detection of ROIs includes: applying a predetermined automatic detection algorithm to the received images to detect a location that has or is suspected to have items of interest such as a lesion; and determining an area surrounding the location. Examples of the automatic detection algorithm may include AdaBoost, Deformable Part models (DPM), Deep Neural Network (DNN), Convolutional Neural Network (CNN), Sparse coding, and the like.

Further, the determination of an ROI includes: measuring the size of an ROI, characteristics of an ROI, such as a shape, an echo pattern, an orientation, a boundary, a texture, an intensity, and the like, or characteristics of a lesion according to Breast Imaging Reporting And Data System (BI-RADS) or Liver imaging Reporting And Data System (LI-RADS) lexicon classification; and by using the measured values, determining whether a lesion is malignant or benign.

In an exemplary embodiment, once images are received by using a probe, the automatic diagnoser 120 may generate diagnosis information by performing automatic diagnosis in parallel with a user's manual diagnosis. In this case, the diagnosis information may include results of each automatic diagnosis, e.g., locations, sizes, characteristics of items of interest, BI-RADS characteristics, LI-RADS characteristics, and determinations of benignancy or malignancy. Further, the diagnosis information may further include Doppler images, ultrasonic elasticity images, anatomical charts, an examination history of a subject, images of a subject's body parts that are acquired by other devices, and information on similar cases.

Further, in another exemplary embodiment, once images are received by using a probe, the automatic diagnoser 120 may perform automatic diagnosis based on a user's manual diagnosis. In this case, a computational subject, accuracy and computational complexity of the automatic diagnosis may vary depending on a user's manual diagnosis.

For example, when a user detects an ROI, the automatic diagnoser 120 may automatically detect an ROI in response thereto. Further, when a user observes the detected ROI, the automatic diagnoser 120 may automatically determine an ROI in response thereto. In this case, the observing process of an ROI may be divided into sub-processes, such as segmentation, characteristic extraction, BI-RADS characteristic extraction and classification, and determination of benignancy or malignancy, and the automatic diagnoser 120 may automatically perform sub-processes of a determination process of an ROI that correspond to sub-processes of the observing process of an ROI.

The information determiner 130 may determine diagnosis information regarding the manual diagnosis that is currently performed by a user and to be output on a screen. In this case, once a user's manual diagnosis is determined, the information determiner 130 may refer to predetermined information as shown in Table 1 below, to determine diagnosis information regarding the determined manual diagnosis to be information to be output on a screen.

The following Table 1 shows an example of predetermined information that includes the types of diagnosis information to be output on a screen for each manual diagnosis of a user; information on whether each type of diagnosis information is output, an output time, an output order, and the like. In this case, the information on whether each type of diagnosis information is output, the output time, and the output order may be predetermined according to a subject to be diagnosed, a diagnosis object, a degree of interest of a user, a predetermined unit time, the speed of a probe, a user's input signal, and the like.

TABLE 1

| Manual diagnosis | Diagnosis information to be output | Information on whether diagnosis information is output | Output time | Output order |
| --- | --- | --- | --- | --- |
| Process for detection of ROI | Information on detection of ROI | Y | — | — |
| Process for observation of ROI | Information on classification of ROI | Y | 5 sec. | 1 |
| | Doppler images | N | 2 sec. | 2 |
| | Ultrasonic elasticity images | N | 2 sec. | 3 |
| | Examination history | Y | 3 sec. | 4 |
| | Similar cases | Y | 3 sec. | 5 |

Referring to Table 1 above, when manual diagnosis that is currently performed by a user is a process for detection of an ROI, the information determiner 130 may determine information, such as ROI location information, which is related to the detection of an ROI detected by the automatic diagnoser 120, to be diagnosis information to be output on a screen.

When manual diagnosis that is currently performed by a user is a process for observation of an ROI, the information determiner 130 may determine information on classification of an ROI, an examination history, and similar cases, which are indicated as "Y" in terms of whether the types of information have been output, to be information to be output on a screen, among information on classification of an ROI, Doppler images, ultrasonic elasticity images, an examination history of a subject, and similar cases.

Based on a predetermined output order and output time, the information determiner 130 may determine information on classification of an ROI, an examination history, and similar cases to be diagnosis information to be output in this order for 5 seconds, 3 seconds, and 3 seconds, respectively, during the process for observation of an ROI. In this case, even after each type of information is output in sequence, the information may be output again when a user performs the process for observation of the ROI.

As Table 1 above is an example, the present disclosure is not limited thereto, and a user may sub-divide information on classification of an ROI into segmentation information, size information of an ROI, characteristic information, characteristics according to BI-RADS lexicon classification and results of the classification, characteristics according to LI-RADS lexicon classification and results of the classification, determination results of benignancy or malignancy, and the like. Further, a user may determine information on whether each type of information has been output, an output time, an output order for each type of information, and the like. In addition, without setting an output time separately for each type of diagnosis information, a user may determine information to be output for an equal period of time (e.g., one second, two seconds, etc.).

In another exemplary embodiment, the information determiner 130 may determine diagnosis information to be output on a screen based on the speed a probe or a signal input from a user through an interface device. An exemplary embodiment will be described in detail later with reference to FIGS. 2 and 3.

The display 140 outputs, on a screen, diagnosis information determined by the information determiner 130 regarding manual diagnosis that is currently performed by a user.

For example, once a user detects an ROI, and the information determiner 130 determines information on the detection of the ROI to be diagnosis information to be output on a screen, the display 140 may display, in an image output on a screen, a distinguished marker that visually indicates an ROI, by using location information of the ROI included in the information on the detection of the ROI. In this case, the distinguished marker may be a bounding box, a circle, an oval, a cross, an arrow, and the like, and may have boundaries with different thicknesses, colors, or the like, to enable a user to easily identify an ROI.

Further, once a user observes an ROI, the display 140 outputs diagnosis information determined by the information determiner 130.

The display 140 may overlay diagnosis information on an image received by the image receiver 110, and may sequentially output each type of diagnosis information according to an output order of the diagnosis information by scrolling the information along with the received image. Alternatively, the display 140 may divide, according to a user' setting, a screen into a first area for outputting a received image and a second area for outputting diagnosis information. The display 140 may overlay a current image with diagnosis results (e.g., information on detection and determination of ROIs) regarding the current image to output the diagnosis results in the first area, and to output diagnosis information (e.g., examination history, similar cases, etc.) to be compared with the diagnosis results regarding the current image in the second area at the same time as the diagnosis results of the current image or at a different time therefrom.

The display 140 may also output, to the second area, diagnosis information (e.g., examination history, information on similar cases, etc.) to be compared with the diagnosis information of a current image at the same time as the diagnosis information of a current image or at a different time therefrom.

Figure 2:
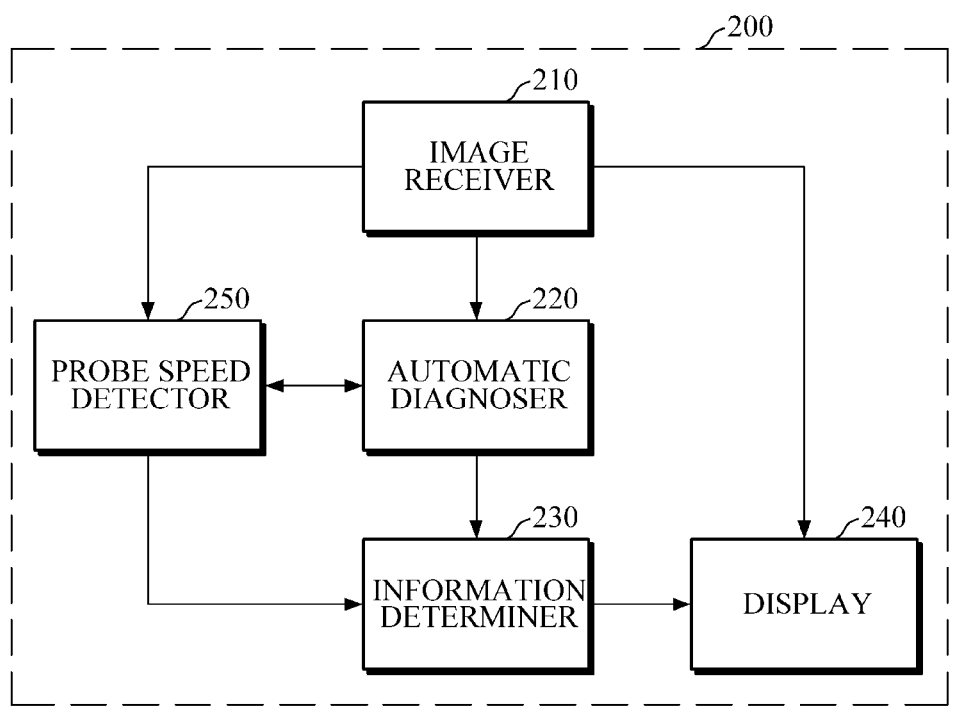
FIG. 2 is a block diagram illustrating a CAD apparatus, according to another exemplary embodiment.

FIG. 2 is a block diagram illustrating a CAD apparatus 200, according to another exemplary embodiment.

Referring to FIG. 2, the CAD apparatus 200 includes an image receiver 210, an automatic diagnoser 220, an information determiner 230, a display 240, and a probe speed detector 250. The image receiver 210, the automatic diagnoser 220, the information determiner 230, and the display 240 are identical to the components 110, 120, 130, and 140 of the CAD apparatus 100 illustrated in FIG. 1, such that the descriptions below will be focused on the probe speed detector 250.

Once a user moves a probe to acquire images of a subject, the probe speed detector 250 detects the speed of the probe.

In an exemplary embodiment, the probe speed detector 250 may detect the speed of a probe by using a change in images received by the image receiver 210, i.e., by calculating an optical flow from a previous frame to a current frame, or by using a difference image between a previous frame and a current frame.

For example, the probe speed detector 250 may detect the speed of a probe by using, as a change in images, a difference between the sum of image intensities for pixels of a previous image frame and the sum of image intensities for pixels of a current image frame acquired through a probe. That is, once an image frame is acquired by a probe, the probe speed detector 250 may preprocess the image frame to measure an image intensity for pixels, and may calculate displacement during a predetermined period of time by using the measured image intensity, to detect the speed of a probe based on the calculated displacement.

In another example, the probe speed detector 250 may detect the speed of a probe based on a difference or similarity between histograms of a previous image frame and a current image frame. In this case, the probe speed detector 250 may generate histograms of each frame using frequency of pixel values extracted from the entire area or an area of a frame, and may detect the speed of a probe based on a frequency difference between the generated histograms or based on a difference or similarity of histograms when the frequency difference between the generated histograms or the similarity of histograms is above a predetermined value.

In yet another example, the probe speed detector 250 may detect the speed of a probe based on change in information such as information on salient regions of a previous frame and a current frame.

In another exemplary embodiment, a probe may include a sensor for measuring a speed, such as a three-axis accelerometer sensor and the like, and the probe speed detector 250 may use the sensor mounted in the probe to detect the probe speed.

Once the probe speed is detected, the probe speed detector 250 may determine, based on the speed, manual diagnosis which is currently performed by a user. In this case, the probe speed detector 250 may determine a user's manual diagnosis by referring to information on the user's manual diagnosis predetermined for each speed of a probe.

In an exemplary embodiment, Table 2 below shows that the probe speed detector 250 may compare a detected probe speed to a predetermined threshold to determine the speed to be either low or high, and based on the probe speed, may determine manual diagnosis to be either a process for observation of an ROI or a process for detection of an ROI.

TABLE 2

| Speed of probe | Speed threshold (cm/sec.) | User's manual diagnosis |
| --- | --- | --- |
| Low speed | Lower than 3 | Process for observation of ROI |
| High speed | 3 or higher | Process for detection of ROI |

In another exemplary embodiment, Table 3 below shows that the probe speed detector 250 may determine the probe speed to be any one of stop, low, or high, and based on the determined probe speed, may determine a user's manual diagnosis to be any one of a process of checking comparison information, a process of checking classification information, and a process of detecting an ROI. The process of checking comparison information includes checking diagnosis information, such as an examination history of a subject or information on similar cases, in comparison with diagnosis results of a current image. The process of checking classification information includes checking, as classification results of a current image, segmentation information, the size of an ROI, characteristic information, determination of benignancy or malignancy, and the like.

TABLE 3

| Speed of probe | Speed threshold (cm/sec.) | User's manual diagnosis |
| --- | --- | --- |
| Stop | Lower than 0.5 | Checking comparison information |
| Low speed | 0.5 to 3 | Checking determination information |
| High speed | 3 or higher | Detecting ROI |

In yet another exemplary embodiment, the probe speed may be subdivided into a first, a second, . . . , and an n-th step, in which the first step may be matched to a process for detection of an ROI. Other steps may be matched to a process for observation of an ROI, in which the process for observation of an ROI is subdivided into a process of checking segmentation, a process of checking characteristic information, a process of checking classification results, a process of checking Doppler images, a process of checking ultrasonic elasticity images, a process of checking examination history, a process of checking similar cases, and the like, which are matched to each of the steps.

Once the image receiver 210 receives an image by using a probe, the automatic diagnoser 220 performs automatic diagnosis using the received image. As described above, the automatic diagnoser 220 may perform automatic diagnosis in parallel with the determination of the probe speed and a user's manual diagnosis, which are determined by the probe speed detector 250. Further, the automatic diagnoser 220 may perform automatic diagnosis in response to a user's manual diagnosis determined by the probe speed detector 250.

Once manual diagnosis that is currently performed by a user is determined according to the speed of a probe, the information determiner 230 may determine diagnosis information that corresponds to the determined manual diagnosis to be diagnosis information to be output on a screen. In this case, as shown in Table 1, the information determiner 230 may determine diagnosis information that corresponds to a user's manual diagnosis by reference to predetermined information. As described above, when a user moves or stops a probe at a low speed for an extended period of time and performs a process for observation of an ROI for an extended duration, the information determiner 230 may determine to output each type of the diagnosis information by scrolling the information sequentially according to an output order and output time of the diagnosis information included in ROI observation information.

The display 240 outputs, on a screen, diagnosis information determined by the information determiner 230, in which the diagnosis information corresponds to manual diagnosis that is currently performed by a user.

Accordingly, a user moves a probe at a high speed so that only the information on the detection of an ROI may be displayed on a screen to determine whether the detected ROI is an ROI to be diagnosed by a user. Further, if the detected ROI is an ROI to be diagnosed, a user may move a probe at a low speed so that information on the observation of an ROI may be output on a screen, in which each type of the diagnosis information included in the ROI observation information may be displayed by sequentially scrolling the information, thereby enabling detailed observation of an ROI.

Figure 3:
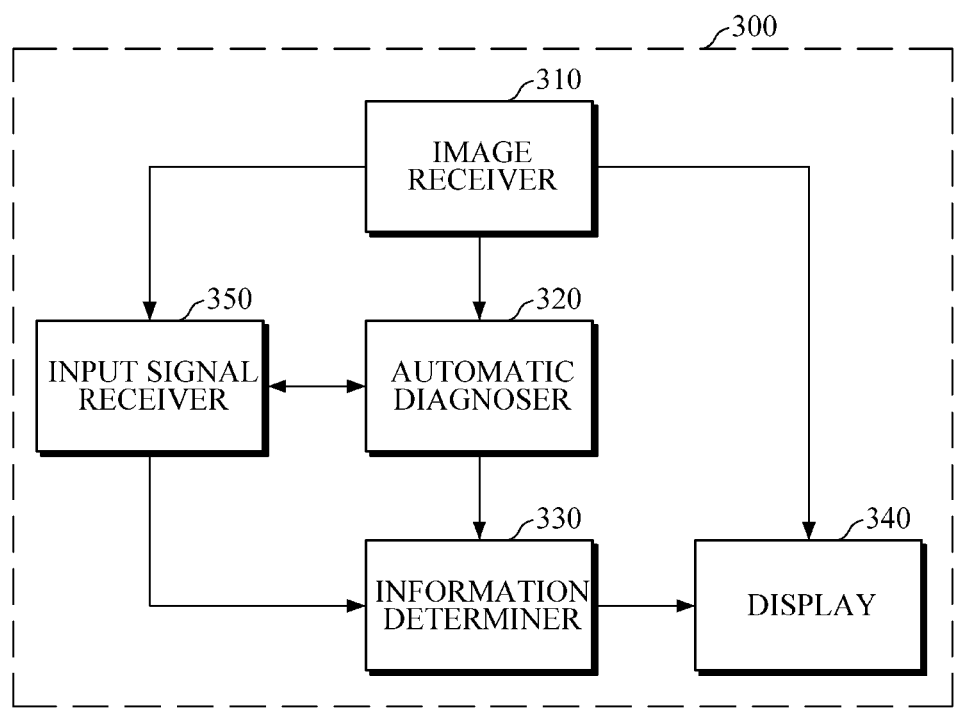
FIG. 3 is a block diagram illustrating a CAD apparatus, according to yet another exemplary embodiment.

FIG. 3 is a block diagram illustrating a CAD apparatus 300, according to yet another exemplary embodiment.

Referring to FIG. 3, the CAD apparatus 300 includes an image receiver 310, an automatic diagnoser 320, an information determiner 330, a display 340, and an input signal receiver 350. In this case, the image receiver 310, the automatic diagnoser 320, the information determiner 330, and the display 340 are identical to the components 110, 120, 130, and 140 of the CAD apparatus 100 illustrated in FIG. 1, such that the descriptions below will be focused on the input signal receiver 350.

The input signal receiver 350 may receive a signal input from a user by using an interface device, and may determine a user's manual diagnosis according to the received input signal.

In this case, the interface device may be an external device that is mounted on the CAD apparatus 300, or may be an external device that is connected through wired or wireless communications, and may include a switch, a jog shuttle, a joy stick, and the like that may be manipulated by a body part, e.g., a left hand/a right foot for a right-handed person (and vice versa for a left-handed person), which is not used to operate a probe. However, the interface device is not limited thereto, and may include various devices, such as a hair band type worn on the head, a glasses type worn on the face, a bracelet type worn on a wrist, an ankle bracelet type worn on an ankle, a ring type worn on a finger.

For example, Table 4 shows a user's manual diagnosis according to the number of signals input from a user within a unit time period. By referring to Table 4 below, the input signal receiver 350 may determine manual diagnosis that is currently performed by a user.

TABLE 4

| The number of input signals | User's manual diagnosis |
|---|---|
| Once | Process for detection of ROI |
| Twice | Process for observation of ROI |

Referring to Table 4 above, once a user inputs a signal once within a unit time (e.g., one sec.) through an interface device, the input signal receiver 350 may determine that a user performs a process for detection of an ROI. As described above, based on the determination made by the input signal receiver 350, the information determiner 330 determines information on the detection of an ROI detected by the automatic diagnoser 320 to be diagnosis information to be output on a screen, and by using ROI location information, the display 340 may overlay a distinguished marker that indicates the location of an ROI on an image.

Then, once a user inputs a signal twice within a unit time through an interface device, the input signal receiver 350 determines that a user performs a process for observation of an ROI, and the display 340 outputs observation information of an ROI on a screen in the same manner as above.

In this case, as shown in Table 1 above, the information determiner 330 may change diagnosis information to be output on a screen during the process for observation of an ROI and diagnosis information to be output on a screen based on an output order and an output time of each diagnosis information. Based on the determination made by the information determiner 330, the display 340 may sequentially output the determined diagnosis information on a screen.

In another example, a user inputs a signal twice to start the process for observation of an ROI, and then when a signal is input once, each diagnosis information included in the ROI observation information may be sequentially output. In this case, once the input signal receiver 350 receives a signal three times from a user, the display 340 deletes information that is currently output on a screen, and may output a subsequent image received by the image receiver 310.

A user's manual diagnosis based on the number of input signals may be changed in various manners, and a user's manual diagnosis may be predetermined based on the length or strength of an input signal and according to the types of interface devices.

Figure 4A:
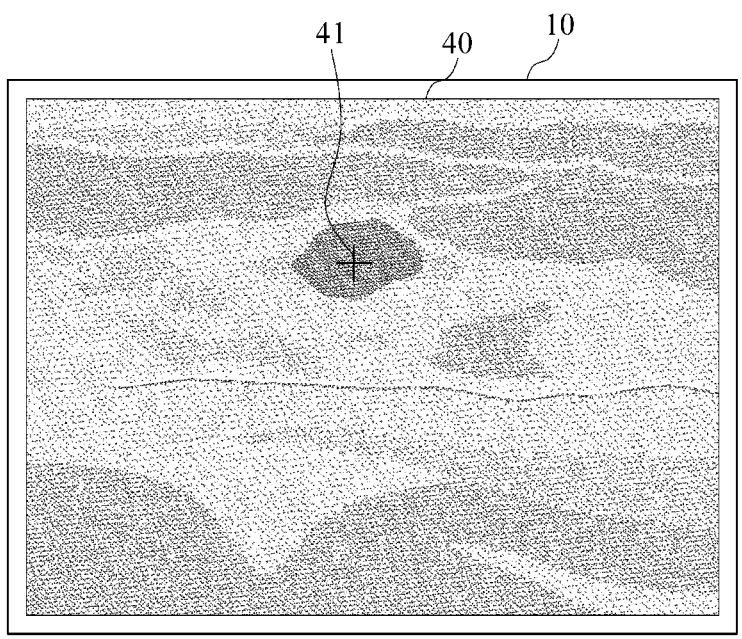
FIGS. 4A and 4B are diagrams illustrating diagnosis information output on a screen in response to a user's manual diagnosis, according to an exemplary embodiment.
Figure 4B:
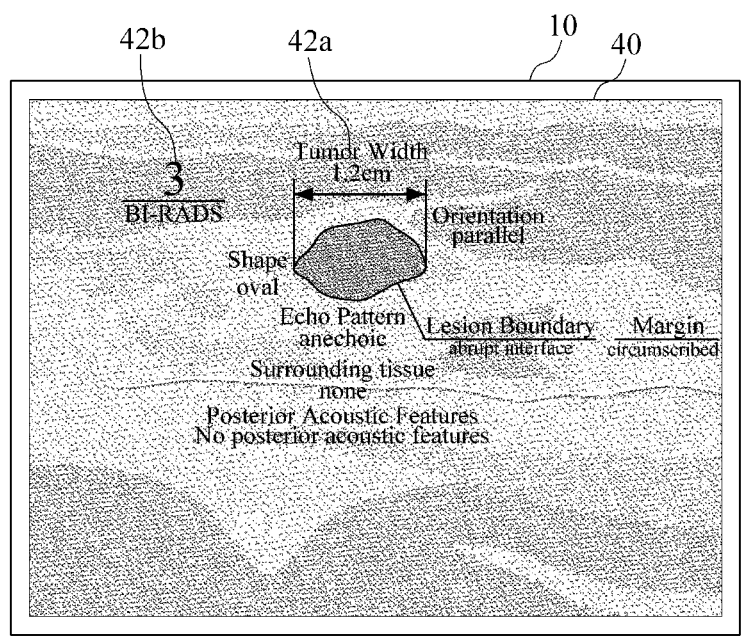
Figure 5A:
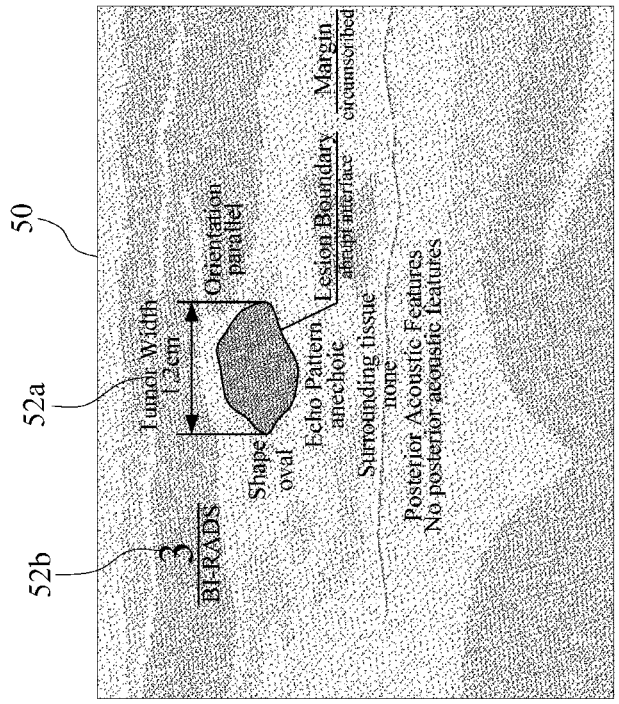
FIGS. 5A and 5B are diagrams illustrating diagnosis information output on a screen in response to the user's manual diagnosis in FIG. 4B.
Figure 5A:
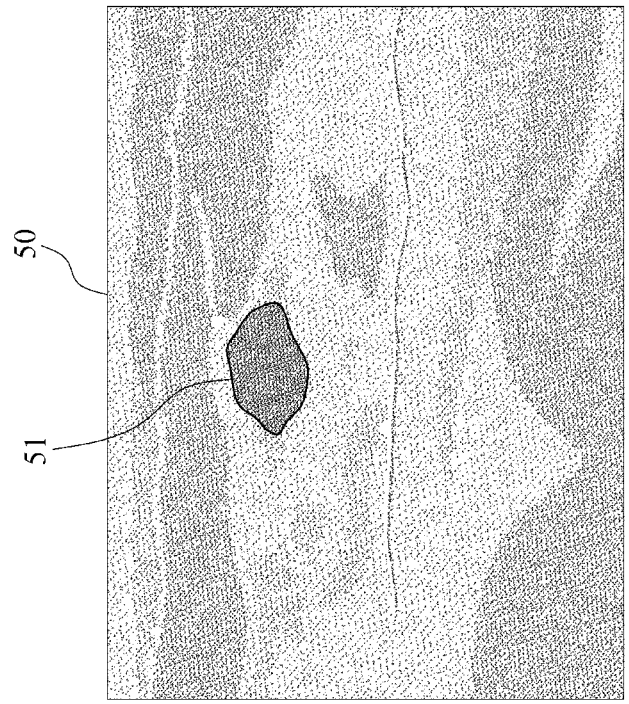
Figure 5B:
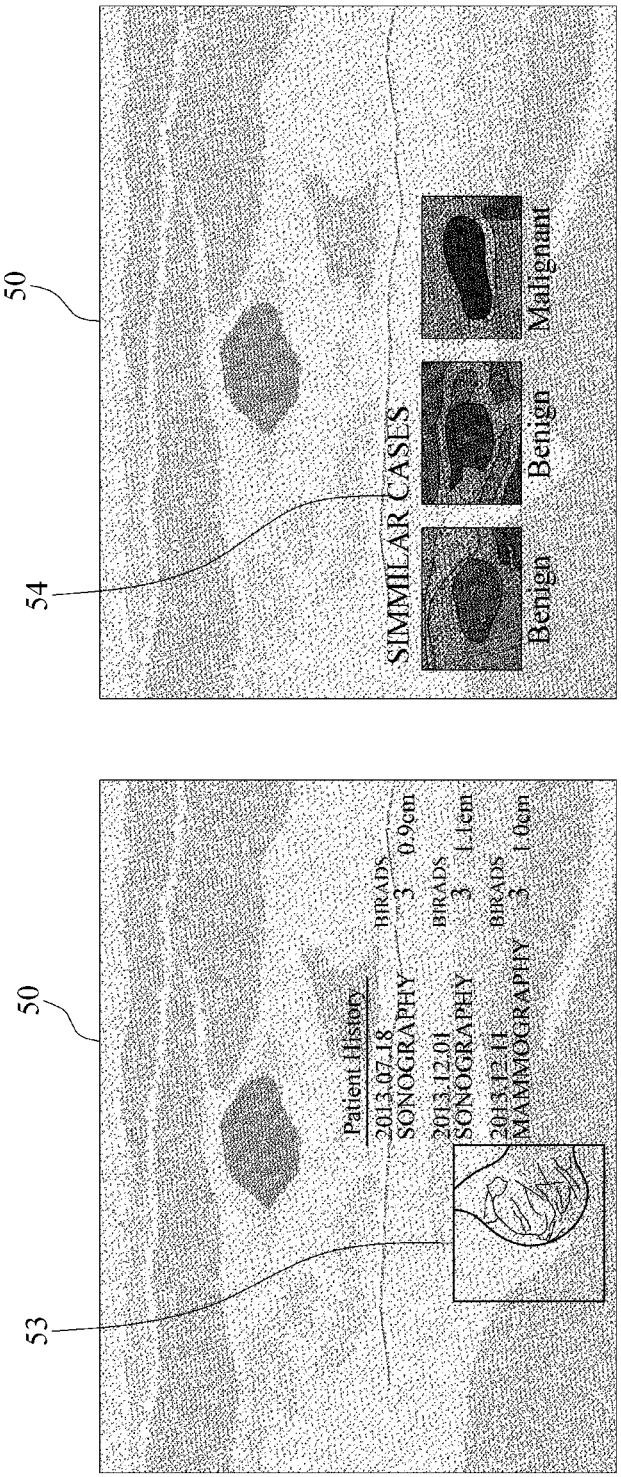

FIGS. 4A and 4B are diagrams illustrating diagnosis information output on a screen 10 in response to a user's manual diagnosis, according to an exemplary embodiment. FIGS. 5A and 5B are diagrams illustrating diagnosis information output on the screen 10 in response to the user's manual diagnosis in FIG. 4B.

As illustrated in FIG. 4A, once manual diagnosis that is currently performed by a user is determined to be a process for detection of an ROI, the CAD apparatus 100, 200, or 300 outputs an image 40 received from a probe on the screen 10, overlays a distinguished marker 41, which indicates an ROI, on the image 40, and outputs the distinguished marker 41. The distinguished marker 41 is not limited to a cross, and may be a bounding box, a circle, an oval, an arrow, and the like.

As illustrated in FIG. 4B, once manual diagnosis that is currently performed by a user is determined to be a process for observation of an ROI, the CAD apparatus 100, 200, or 300 outputs the image 40 received from a probe on the screen 10, and overlays classification information of an ROI on the image 40 that includes a size 42a of a lesion, a BI-RADS classification result 42b, segmentation information, lesion characteristic information, and the like. In this case, the CAD apparatus 100, 200, or 300 may output all the classification information of an ROI at the same time on a screen, or may sequentially scroll the classification information based on a predetermined output order and a predetermined output time of the diagnosis information.

FIGS. 5A and 5B are diagrams illustrating an example of ROI observation information that may be output on a screen when the CAD apparatus 100, 200, or 300 performs a process for observation of an ROI as illustrated in FIG. 4B. Referring to FIGS. 5A and 5B, once it is determined that a user performs a process for observation of an ROI, the CAD apparatus 100, 200, or 300 sequentially outputs, on a screen 50, (a) ROI segmentation information 51; (b) classification information that includes a size 52a of a lesion, a BI-RADS classification results 52b, and the like; (c) an examination history of a patient, and an image 53 of an identical region that is acquired by other devices; and (d) information 54 of similar cases of the patient.

Figure 6:
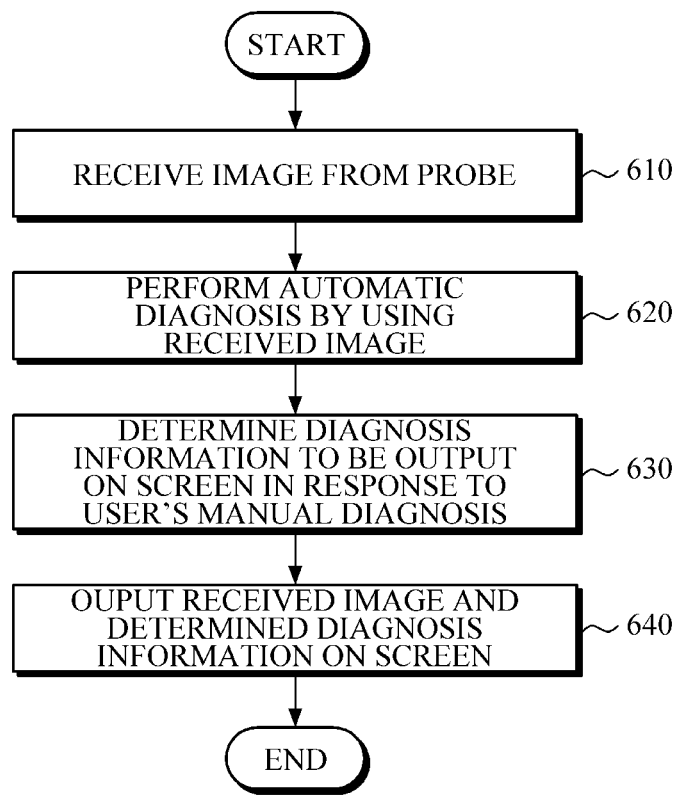
FIG. 6 is a flowchart illustrating a CAD method, according to an exemplary embodiment.

FIG. 6 is a flowchart illustrating a CAD method, according to an exemplary embodiment. FIG. 6 illustrates an example of a CAD method performed by the CAD apparatus 100 illustrated in FIG. 1.

In operation 610, the CAD apparatus 100 receives an image from a probe. In this case, the image is acquired through the probe in real time, and may be input to the CAD apparatus 100 in units of frames.

In operation 620, the CAD apparatus 100 performs automatic diagnosis by using the received image. The automatic diagnosis may include: a process for detection of an ROI by applying an automatic detection algorithm to the image; and a process for classification of the detected ROI.

In operation 630, the CAD apparatus 100 determines diagnosis information to be output on a screen in response to a user's manual diagnosis that is currently performed. As shown in Table 1 above, based on a subject to be diagnosed, a diagnosis purpose, a probe speed, a signal input through an interface device, and the like, the types of diagnosis information to be output on a screen, information on whether each type of the diagnosis information is output, an output time, an output order, and the like may be predetermined for each process of the manual diagnosis.

By referring to the predetermined information, the CAD apparatus 100 may determine ROI detection information to be diagnosis information to be output on a screen when a user's manual diagnosis is a process for detection of an ROI. Further, when a user's manual diagnosis is a process for observation of an ROI, the CAD apparatus 100 may determine ROI observation information to be diagnosis information to be output on a screen. In this case, by referring to predetermined information on whether the ROI observation information is output while the process for observation of an ROI is performed, the CAD apparatus 100 may determine one or more types of diagnosis information to be output among the ROI observation information.

In operation 640, the CAD apparatus 100 outputs the received image and the determined diagnosis information on the screen. For example, once a user performs a process for detection of an ROI, a distinguished marker that visually indicates an ROI may be displayed in an image output on a screen by using ROI location information. Further, once a user performs a process for observation of an ROI, the determined diagnosis information, e.g., segmentation, the size of an ROI, characteristic information, determination of benignancy or malignancy, BI-RADS classification results, and the like may be overlaid on an image to be scrolled on a screen. In this case, a type of the diagnosis information may be displayed in a separate area of a screen without being overlaid on an image, so that a user may easily compare diagnosis results of a current image with the diagnosis information.

Figure 7:
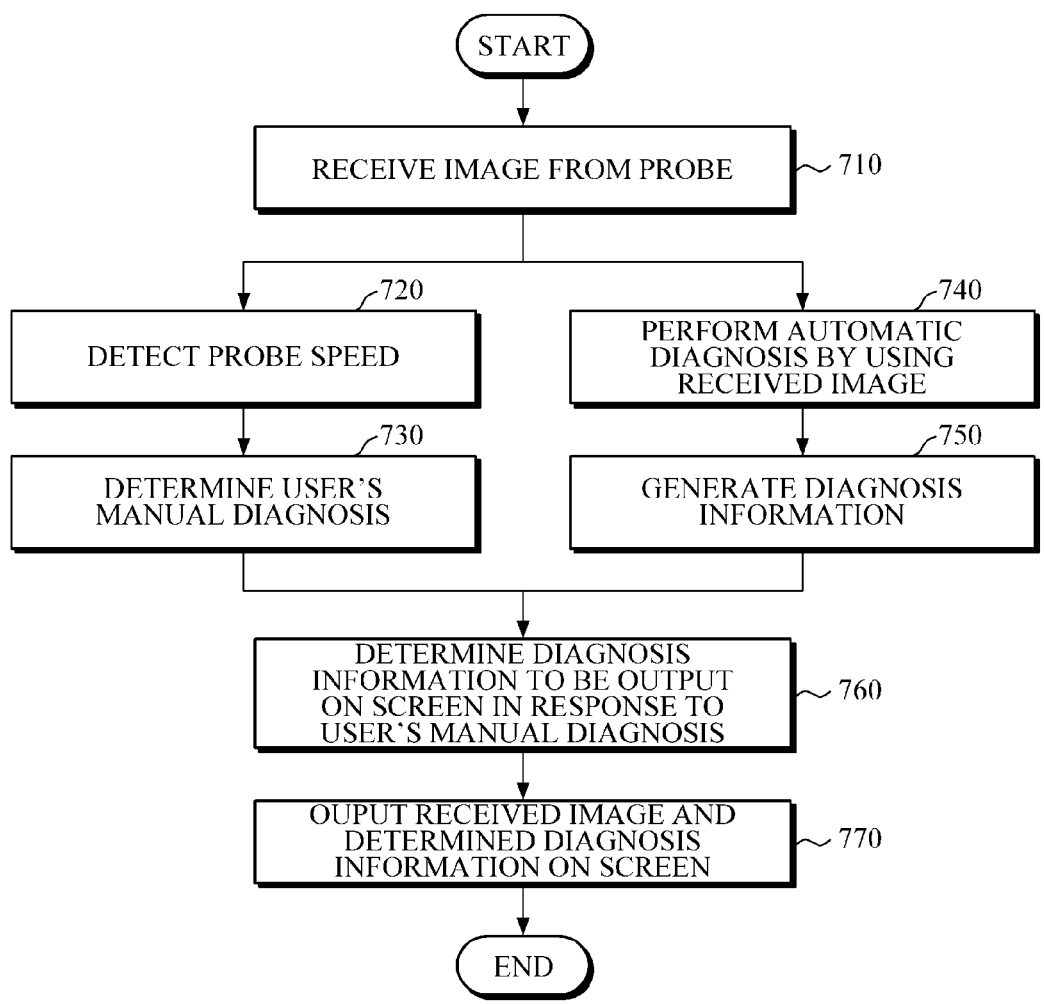
FIG. 7 is a flowchart illustrating a CAD method, according to another exemplary embodiment.

FIG. 7 is a flowchart illustrating a CAD method, according to another exemplary embodiment. FIG. 7 illustrates an example of a CAD method performed by the CAD apparatus 200 illustrated in FIG. 2.

In operation 710, the CAD apparatus 200 receives an image from a probe.

In operation 720, the CAD apparatus 200 detects a speed of the probe used by a user to acquire the image. In this case, the probe speed may be detected by calculating a change in received images, i.e., an optical flow from a previous frame to a current frame, or by using a difference image between a previous frame and a current frame.

For example, the probe speed may be detected by using, as a change in images, a difference between the sum of image intensities for pixels of a previous image frame and the sum of image intensities for pixels of a current image frame acquired through a probe. Further, the probe speed may be detected based on a difference or similarity between histograms of a previous image frame and a current image frame. Alternatively, the probe speed may be detected based on a change in information of salient regions of a previous frame and a current frame, or by using a speed measuring sensor mounted on a probe.

In operation 730, the CAD apparatus 200 determines the user's manual diagnosis that is currently performed, based on the detected probe speed. In an exemplary embodiment, as shown in Table 2 above, the CAD apparatus 200 may determine the detected probe speed to be either high or low, and based on the probe speed, may determine manual diagnosis to be either a process for observation of an ROI or a process for detection of an ROI. In another exemplary embodiment, as shown in Table 3 above, the CAD apparatus 200 may determine the speed of a probe to be any one of stop, low, or high, and based on the determined probe speed, may determine a user's manual diagnosis to be any one of a process of checking comparison information, a process of checking determination information, and a process of detecting an ROI. In this case, the probe speed and a user's manual diagnosis are not limited to the above exemplary embodiments, and may be determined in various manners.

In operation 740, the CAD apparatus 200 performs automatic diagnosis using the received image. As illustrated in FIG. 7, the automatic diagnosis may be performed in parallel with the detection of the probe speed in operation 720 and the determination of the user's manual diagnosis in operation 730. In another exemplary embodiment, automatic diagnosis may be performed in response to the user's manual diagnosis determined in operation 730 based on the detection of the probe speed in operation 720.

In operation 750, the CAD apparatus 200 generates diagnosis information that includes results of the automatic diagnosis. The diagnosis information refers to results of diagnosis performed by using a current image, includes information on detection of an ROI and classification of an ROI, and may further include Doppler images, ultrasonic elasticity images, an examination history of a subject, information on similar cases, and the like.

In operation 760, the CAD apparatus 200 determines diagnosis information to be output on a screen in response to the user's manual diagnosis, among the generated diagnosis information. For example, when a user moves a probe at a high speed for the process of detection of an ROI, the information on the detection of an ROI, which is detected by automatic diagnosis, is determined to be diagnosis information to be output on a screen. Further, when a user moves a probe at a low speed for the process of observation of an ROI, information on classification of an ROI, Doppler images, ultrasonic elasticity images, an examination history, similar cases, and the like may be determined to be diagnosis information to be output on a screen. In this case, if a user performs the process for observation of an ROI for an extended duration, each type of the diagnosis information may be displayed by sequentially scrolling the information according to a predetermined output order and a predetermined output time.

In operation 770, the CAD apparatus 200 outputs the received image and the determined diagnosis information on the screen, in which the determined diagnosis information may be overlaid on the received image, or may be output in other areas on the screen where the received image is not output.

FIG. 8 is a flowchart illustrating a CAD method, according to yet another exemplary embodiment. FIG. 8 illustrates an example of a CAD method performed by the CAD apparatus 300 illustrated in FIG. 3.

In operation 810, the CAD apparatus 300 receives an image from a probe.

In operation 820, the CAD apparatus 300 receives an input signal from a user through an interface device. In this case, the interface device is an external device that is mounted in the CAD apparatus 300 or an external device that is connected through wired or wireless communications, and may include a switch, a jog shuttle, a joy stick, and the like. However, the interface device is not limited thereto, and may include a signal generating device that is manufactured in various manners, such as a hair band, glasses, a bracelet, an ankle, a ring, and the like.

In operation 830, the CAD apparatus 300 determines the user's manual diagnosis that is currently performed, based on the received input signal. In this case, a user's manual diagnosis may be predetermined according to the number of input signals as shown in Table 4 above.

Once the received image is output on a screen, a user may input a signal once to transmit an intention to perform the process for detection of an ROI to the CAD apparatus 300. Further, a user may input a signal twice within a unit time to transmit an intention to perform the process for observation of an ROI to the CAD apparatus 300, in which the process for observation of an ROI includes a process of checking classification results of an ROI, and the like. The above exemplary embodiments are illustrative, and one or more exemplary embodiments may also be realized.

In operation 840, the CAD apparatus 300 performs automatic diagnosis by using the received image. As illustrated in FIG. 8, the automatic diagnosis may be performed in parallel with the reception of the input signal from the user in operation 820 and the determination of the user's manual diagnosis in operation 830. Alternatively, the automatic diagnosis may be performed in response to the user's manual diagnosis determined in operation 830.

In operation 850, the CAD apparatus 300 generates diagnosis information that includes results of the automatic diagnosis. The diagnosis information may include information on detection and observation of an ROI, in which the ROI observation information may include ROI classification information, Doppler images, ultrasonic elasticity images, an examination history of a subject, information on similar cases, and the like.

In operation 860, the CAD apparatus 300 determines diagnosis information to be output on the screen in response to the user's manual diagnosis among the generated diagnostic information.

In operation 870, the CAD apparatus 300 outputs the received image and the determined diagnosis information on the screen.

In addition, the exemplary embodiments may also be implemented through computer-readable code and/or instructions on a medium, e.g., a computer-readable medium, to control at least one processing element to implement any above-described exemplary embodiments. The medium may correspond to any medium or media which may serve as a storage and/or perform transmission of the computer-readable code.

The computer-readable code may be recorded and/or transferred on a medium in a variety of ways, and examples of the medium include recording media, such as magnetic storage media (e.g., ROM, floppy disks, hard disks, etc.) and optical recording media (e.g., compact disc read only memories (CD-ROMs) or digital versatile discs (DVDs)), and transmission media such as Internet transmission media. Thus, the medium may have a structure suitable for storing or carrying a signal or information, such as a device carrying a bitstream according to one or more exemplary embodiments. The medium may also be on a distributed network, so that the computer-readable code is stored and/or transferred on the medium and executed in a distributed fashion. Furthermore, the processing element may include a processor or a computer processor, and the processing element may be distributed and/or included in a single device.

The foregoing exemplary embodiments are examples and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A Computer-Aided Diagnosis (CAD) apparatus, comprising:
    a display; and
    a processor configured to:
        control to display, through the display, an image being received from a probe;
        perform an automatic diagnosis, using the image being;
        generate diagnosis information comprising results of the automatic diagnosis;
        control to detect a user input on the image being displayed;
        determine a movement speed of the user input that is detected;
        determine a type of a manual diagnosis, based on the movement speed that is determined;
        determine a portion of the diagnosis information to be displayed through the display, based on the type of the manual diagnosis that is determined; and
        control to display, through the display, the portion of the diagnosis information that is determined, the portion of the diagnosis information being superimposed on the image being displayed.

2. The CAD apparatus of claim 1, wherein the user input is for a first process for detection of a region of interest (ROI) or a second process for observation of the ROI that is detected, and
    the portion of the diagnosis information is further determined based on the user input that is detected.

3. The CAD apparatus of claim 2, wherein, based on the user input that is detected being for the first process for the detection of the ROI, the portion of the diagnosis information is determined to include first information regarding the detection of the ROI, and
    based on the user input that is detected being for the second process for the observation of the ROI that is detected, the portion of the diagnosis information is determined to include second information regarding the observation of the ROI that is detected.

4. The CAD apparatus of claim 3, wherein the first information regarding the detection of the ROI included in the portion of the diagnosis information being displayed is highlighted relative to the image being displayed.

5. The CAD apparatus of claim 3, wherein the second information regarding the observation of the ROI that is detected included in the portion of the diagnosis information being displayed is changed based on a type of the observation of the ROI that is detected and an output order of the observation of the ROI that is detected.

6. The CAD apparatus of claim 5, wherein the processor is further configured to determine the type of the observation of the ROI that is detected and the output order of the observation of the ROI that is detected, based on one or more of the movement speed that is determined and a number of the user input that is detected.

7. The CAD apparatus of claim 5, wherein the type of the observation of the ROI that is detected comprises ROI classification information indicating a degree of benignancy or malignancy of the ROI that is detected.

8. The CAD apparatus of claim 1, wherein the movement speed of the user input that is detected is determined based on a change of the image being displayed, and
the change of the image comprises any one or any combination of a first difference between a first image intensity of a first pixel in the image, a second difference between a first histogram of a previous frame in the image and a second histogram of a current frame in the images, a similarity between the first histogram and the second histogram and a change of information of salient regions of the image.

9. The CAD apparatus of claim 1, wherein the processor is further configured to perform the automatic diagnosis while detecting the user input.

10. The CAD apparatus of claim 1, wherein the type of the manual diagnosis comprises a first process for detection of a region of interest (ROI) in a range and a second process for observation of the ROI that is detected.

11. The CAD apparatus of claim 1, wherein the movement speed of the user input that is detected is determined based on data that is received via an accelerometer sensor of the probe.

12. A Computer-Aided Diagnosis (CAD) method, comprising:
displaying an image being received from a probe;
performing an automatic diagnosis, using the image being displayed;
generating diagnosis information including results of the automatic diagnosis;
detecting a user input on the image being displayed;
determining a movement speed of the user input that is detected;
determining a type of a manual diagnosis, based on the movement speed that is determined;
determining a portion of the diagnosis information to be displayed, based on the type of the manual diagnosis that is determined; and
displaying the portion of the diagnosis information that is determined, the portion of the diagnosis information being superimposed on the image being displayed.

13. The CAD method of claim 12, wherein the user input is for a first process for detection of a region of interest (ROI) or a second process for observation of the ROI that is detected, and
the portion of the diagnosis information is further determined based on the user input that is detected.

14. The CAD method of claim 13, wherein, based on the user input that is detected being for the first process for the detection of the ROI, the portion of the diagnosis information is determined to include first information regarding the detection of the ROI, and
based on the user input that is detected being for the second process for the observation of the ROI that is detected, the portion of the diagnosis information is determined to include second information regarding the observation of the ROI that is detected.

15. The CAD method of claim 13, wherein the first information regarding the detection of the ROI included in the portion of the diagnosis information being displayed is highlighted relative to the image being displayed.

16. The CAD method of claim 13, wherein the second information regarding the observation of the ROI that is detected included in the portion of the diagnosis information being displayed is changed based on a type of the observation of the ROI that is detected and an output order of the observation of the ROI that is detected.

17. The CAD method of claim 12, wherein the type of the manual diagnosis comprises a first process for detection of a region of interest (ROI) in the image and a second process for observation of the ROI that is detected.

18. A non-transitory computer-readable storage medium storing instructions executable by a processor of an electronic device to cause the processor to perform a method, the method comprising:
displaying an image being received from a probe;
performing an automatic diagnosis, using the image being displayed;
generating diagnosis information including results of the automatic diagnosis;
detecting a user input on the image being displayed;
determining a movement speed of the user input that is detected;
determining a type of a manual diagnosis, based on the movement speed that is determined;
determining a portion of the diagnosis information to be displayed, based on the type of the manual diagnosis that is determined; and
displaying the portion of the diagnosis information that is determined, the portion of the diagnosis information being superimposed on the image being displayed.

* * * * *